United States Patent
Foschini et al.

(10) Patent No.: US 9,700,456 B2
(45) Date of Patent: Jul. 11, 2017

(54) DEVICE AND METHOD FOR CORNEAL DELIVERY OF RIBOFLAVIN BY IONTOPHORESIS FOR THE TREATMENT OF KERATOCONUS

(75) Inventors: Fulvio Foschini, Rome (IT); Pierre Roy, Paris (FR); Edoardo Stagni, Catania (IT); Giovanni Cavallo, Rome (IT); Giulio Luciani, Bagno a Ripoli (IT)

(73) Assignee: SOOFT ITALIA SPA, Montegiorgio (IT)

( * ) Notice: Subject to any disclaimer, the term of this patent is extended or adjusted under 35 U.S.C. 154(b) by 1151 days.

(21) Appl. No.: 13/824,850

(22) PCT Filed: Jan. 12, 2011

(86) PCT No.: PCT/IT2011/000009
§ 371 (c)(1),
(2), (4) Date: Mar. 18, 2013

(87) PCT Pub. No.: WO2012/095876
PCT Pub. Date: Jul. 19, 2012

(65) Prior Publication Data
US 2013/0178821 A1    Jul. 11, 2013

(51) Int. Cl.
*A61F 9/00*    (2006.01)
*A61K 31/525*    (2006.01)
(Continued)

(52) U.S. Cl.
CPC .......... *A61F 9/0026* (2013.01); *A61K 31/525* (2013.01); *A61N 1/044* (2013.01);
(Continued)

(58) Field of Classification Search
CPC ... A61F 9/0026; A61F 9/0008; A61N 5/0613; A61N 1/30; A61N 1/0436; A61N 1/044; A61N 1/325; A61N 1/0448; A61K 31/525
(Continued)

(56) References Cited

U.S. PATENT DOCUMENTS

| 3,122,137 A | 2/1964 | Erlanger |
| 4,564,016 A * | 1/1986 | Maurice ................ A61F 9/0017 604/20 |

(Continued)

FOREIGN PATENT DOCUMENTS

| JP | 2007-535353 | 12/2007 |
| JP | 2007-537767 | 12/2007 |

(Continued)

OTHER PUBLICATIONS

International Search Report dated Aug. 2, 2011, in corresponding PCT application.
(Continued)

*Primary Examiner* — Manuel Mendez
(74) *Attorney, Agent, or Firm* — Young & Thompson

(57) ABSTRACT

Ocular iontophoresis device and method for delivering any ionized drug solution to the cornea includes: a reservoir containing a solution suitable to be positioned on the eye; an active electrode disposed in or on the reservoir; and a passive electrode suitable to be placed on the skin of the subject, elsewhere on the body; elements for irradiating the cornea surface with suitable light for obtaining corneal cross-linking after the drug delivery; wherein the reservoir and the active electrode are transparent to UV light and/or visible light and/or IR light. The method includes: positioning the iontophoretic device on the eye to be treated; driving the solution by a cathodic current applied for 0.5 to 5 min, at an intensity not higher than 2 mA; and thereafter irradi-
(Continued)

ating, with UV light for 5 to 30 min at a power of 3 to 30 mW/cm$^2$; thereby obtaining the corneal cross-linking of the solution.

29 Claims, 3 Drawing Sheets

(51) Int. Cl.
| | | |
|---|---|---|
| *A61N 1/04* | (2006.01) | |
| *A61N 1/32* | (2006.01) | |
| *A61N 1/30* | (2006.01) | |
| *A61N 5/06* | (2006.01) | |

(52) U.S. Cl.
CPC ......... *A61N 1/0436* (2013.01); *A61N 1/0448* (2013.01); *A61N 1/30* (2013.01); *A61N 1/325* (2013.01); *A61N 5/0613* (2013.01); *A61F 9/0008* (2013.01)

(58) Field of Classification Search
USPC .............. 604/20, 19, 22, 289, 294, 297–301
See application file for complete search history.

(56) References Cited

U.S. PATENT DOCUMENTS

| | | |
|---|---|---|
| 6,154,671 A | 11/2000 | Parel et al. |
| 6,319,240 B1 | 11/2001 | Beck |
| 6,442,423 B1 | 8/2002 | Domb et al. |
| 7,164,943 B2 | 1/2007 | Roy |
| 2005/0049541 A1* | 3/2005 | Behar .................... A61N 1/306 604/20 |
| 2005/0245856 A1* | 11/2005 | Roy .......................... A61F 9/00 604/20 |
| 2007/0112295 A1* | 5/2007 | Roy ....................... A61F 9/0017 604/20 |

FOREIGN PATENT DOCUMENTS

| | | |
|---|---|---|
| JP | 2012-502668 | 2/2012 |
| WO | 2005-004979 | 1/2005 |
| WO | 2007/025244 | 3/2007 |
| WO | 2009-073213 | 6/2009 |
| WO | 2010/023705 | 8/2009 |
| WO | 2009/158032 | 12/2009 |

OTHER PUBLICATIONS

Prausnitz et al. "Permeability of Cornea, Sclera, and Conjunctiva: A Literature Analysis for Drug Delivery to the Eye", Journal of Pharmaceutical Sciences, 1479 vol. 87, No. 12, Dec. 1998.
Huang et al. "Swelling Studies on the Cornea and Sclera: The Effects of pH and Ionic Strength", Biophysical Journal, vol. 77, pp. 1655-1665, Sep. 1999, Oxford, England.

* cited by examiner

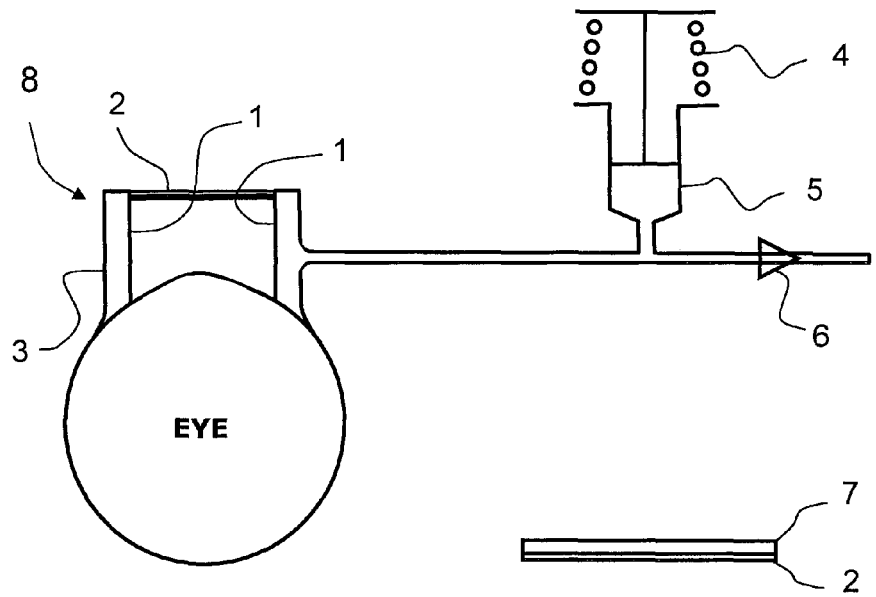
Fig. 1
Fig. 2
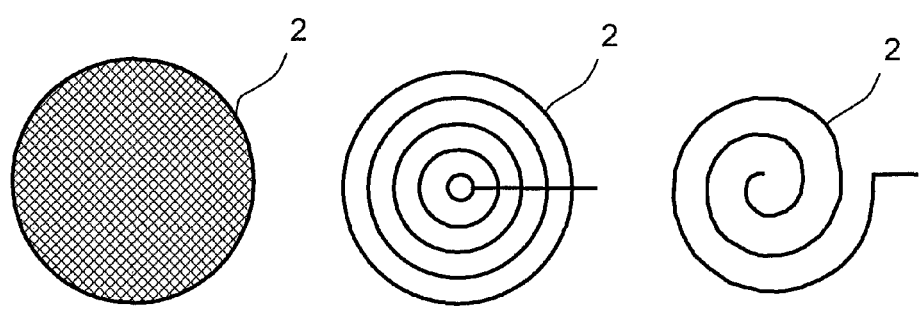
Fig. 3A    Fig. 3B    Fig. 3C

DEVICE AND METHOD FOR CORNEAL DELIVERY OF RIBOFLAVIN BY IONTOPHORESIS FOR THE TREATMENT OF KERATOCONUS

BACKGROUND OF THE INVENTION

Field of the Invention

The present invention relates to a new device for iontophoresis to deliver ophthalmic compositions (in particular collyriums) preferably containing riboflavin, designed to imbibe the corneal stroma without having to proceed, in order to obtain said imbibition, to the removal of the corneal epithelium (de-epithelization) in the practice of the treatment of keratoconus, or other ectasic corneal disorders, by means of corneal cross-linking of suitable ophthalmic composition.

Description of the Related Art

Keratoconus is a degenerative disease of the eye in which structural changes within the cornea cause it to thin and change to a more conical shape than its normal gradual curve. Keratoconus is a genetic disease consisting in a non-inflammatory progressive dystrophy affecting approximately 50 persons in every 100 000 each year, generally young people between 10 and 20 years of age. As disease frequency is higher amongst females, keratoconus etiology appears to be correlated to dysfunctions of endocrine glands (hypophysis and thyroid). It can affect both eyes in approximately 85% of cases and has an evolution that may vary from subject to subject.

Upon onset of this disease, there appears an irregular curvature that modifies the refractive power of the cornea, producing distorsions of images and a confused close and distant vision. The patient complains in any case of a reduction of vision, above all distant vision. The vision continues to regress irreversibly, with a consequent need for frequent change of spectacles, and for this reason it may at first be mistaken for a myopia associated to astigmatism.

On account of the congenital structural weakness of the corneal stroma due to said disease, after some years the cornea progressively tends to wear out and thin out towards the apex. There then occurs an irregular curvature of the cornea, which loses its spherical shape and assumes the characteristic cone shape (keratoconus).

Using the biomicroscope there may be noted a considerable reduction in the corneal thickness at the top of keratoconus. Over time, the top of keratoconus becomes opaque on account of an alteration in the nutriment of that part of the cornea, which in the most acute forms can present a corneal curvature of more than 62D and reach a corneal thickness of even 446 μm (normal central corneal thickness is 500-700 μm).

If the disease is neglected, the top can ulcerate with consequent perforation of the cornea; there appear pain, lacrimation and spasm of the eyelids. These changes of the cornea due to keratoconus produce an alteration in the disposition of the corneal protein, causing micro-scars that further distort the images and in some cases prevent passage of light, thus giving rise to a troublesome dazzling feeling, above all at times of the day when the sun is low on the horizon (sunrise and sunset).

As already mentioned, in order to correct the vision it becomes necessary to change spectacles frequently. Only after the use of spectacles has proven unsatisfactory, in milder forms rigid contact lenses may be applied.

The real problem arises when the cornea affected by keratoconus undergoes considerable thinning or if cicatrization occurs following upon lacerations of the corneal surface, rendering necessary even surgical transplantation of the cornea (keratoplasty).

In 2002 so-called lamellar keratoplasty was introduced in Italy for the treatment of keratoconus, whereby, in practice, not the entire cornea is replaced, but only the outer thickness, i.e., the part affected by the disease.

However, already by 1997 in Germany, in the ophthalmic clinic of the Carl Gustaw Carus University of Dresda, a new safer and less invasive technique was developed, referred to as "corneal cross-linking" (CXL), which uses in particular riboflavin, activated by a UV laser; in 2005 this technique was tested also in Italy and is by now widely used successfully in various Italian eye clinics.

Corneal cross-linking is a minimally-invasive method, which uses riboflavin activated by a UV laser (365-370 nm); the method is painless and is carried out in day-hospital. Cross-linking enables reinforcement of the structure of the cornea affected by keratoconus through the interweaving and increase in links (cross-linking) between the fibers of the corneal collagen. Clinical studies have proved CXL being able to reduce the astigmatism associated to keratoconus as well as to slow down or arrest pathology evolution, thus avoiding the need for transplantation of the cornea. Also other disorders characterized by corneal ecstasia benefit from treatment using the cross-linking method.

Corneal cross-linking is usually carried out by applying a local corneal anaesthesia for making the abrasion of the corneal epithelium (de-epithelization) having a diameter of 8-9 mm. This is followed by a frequent instillation of a 0.1% riboflavin-based ophthalmic solution during 15 minutes, followed by irradiation with ultraviolet (UV-A) emitter during 30 minutes with instillation of riboflavin solution throughout the irradiation operation.

Riboflavin (molecular weight 376, poorly soluble in water), more preferably riboflavin sodium phosphate (molecular weight 456, negatively charged), which is commonly used in corneal cross-linking, is a hydrophilic photosensitizing and photopolymerizing molecule with a poor capacity for diffusing through the epithelium and hence reaching the corneal stroma.

It is therefore necessary to facilitate absorption thereof and complete impregnation of the corneal stroma before starting the irradiation with UV-A, by removing the corneal epithelium (de-epithelization). This procedure can create, albeit rarely, complications at a corneal level, pain, in addition to being a method that renders the task of the ophthalmologist more difficult.

It would hence be desirable to improve the absorption of riboflavin, without having to remove the epithelium of the cornea, hence obtaining a noninvasive corneal cross-linking with elimination or reduction of the anaesthesia and consequent fast healing without pain or possible complications.

Iontophoresis is known as a noninvasive method which allows the penetration of high concentration of ionized molecules, such as drugs, into living tissue driven by an electric current, in fact, applying a current to an ionizable substance increases its mobility across a biological surface. Three principle forces govern the flux caused by the current. The primary force is electrochemical repulsion, which propels species of the same charge through tissues. When an electric current passes through an aqueous solution containing electrolytes and a charged material (for example, the active pharmaceutical ingredient), several events occur:
(1) the electrode generates ions,
(2) the newly generated ions approach/collide with like charged particles (typically the drug being delivered), and
(3) the electrorepulsion between the newly generated ions force the dissolved/suspended charged particles into and/or through the surface adjacent (tissue) to the electrode.

Continuous application of electrical current drives the active pharmaceutical ingredients significantly further into the tissues than is achieved with simple topical administration. The degree of iontophoresis is proportional to the applied current and the treatment time.

Iontophoresis occurs in water-based preparations, where ions can be readily generated by electrodes. Two types of electrodes can be used to produce ions: (1) inert electrodes and (2) active electrodes.

Each type of electrode requires aqueous media containing electrolytes. Iontophoresis with an inert electrode is governed by the extent of water hydrolysis that an applied current can produce. The electrolysis reaction yields either hydroxide $OH^-$ (cathodic) or hydronium $H_3O^+$ (anodic) ions. Some formulations contain buffers, which can mitigate pH shifts caused by these ions. The presence of certain buffers introduces like charged ions that can compete with the drug product for ions generated electrolytically, which can decrease delivery of the drug product (and therefore increase the required application time). The electrical polarity of the drug delivery electrode is dependent on the chemical nature of the drug product, specifically its $pK_a(s)$/isoelectric point and the initial dosing solution pH. It is primarily the electrochemical repulsion between the ions generated via electrolysis and the drug product charge that drives the drug product into tissues. Thus, iontophoresis offers a significant advantage over topical drug application, in that it increases drug absorption. The rate of drug delivery may be adjusted by varying the applied current by the person skilled in the art.

Due to the highly effective administration way of the iontophoretic process, ophthalmologist have long recognized the value of iontophoresis in the delivery of curative molecules to the eye and in the treatment of ocular pathologies, as not only the iontophoretic process permits a more rapid medicine application, but it also allows a more localized and more highly concentrated application of drugs.

Several ocular iontophoretic devices have been developed, reported in the literature and known from the prior art.

The U.S. Pat. No. 3,122,137 filed on Oct. 30, 1961 describes an eye iontophoretic device consisting in a eyeglass frame shaped structure of non-conductive material and incorporating a current source adapted to be supported by the area around the eye orbit, in such a way the device cannot be in direct contact to the eye surface. Such device lacks of substance administration precision due to its rudimentary structural and design features.

The U.S. Pat. No. 4,564,016 filed on Aug. 13, 1984 describes an apparatus having a portion in engagement with the eye, consisting of a small application surface (1 mm diameter) applied on sclera and allowing very high current densities for focal iontophoresis. Such apparatus and the relative method are particularly adapted to introduce ionized drugs into the posterior portion of the eye across the cellular barriers protecting the retina such as the conjunctival epithelium and the pigment epithelium, but the current applied by this method are certainly toxic for the concerned tissues.

More recently, the U.S. Pat. No. 6,319,240 filed on May 25, 1999 proposes an improvement of previous apparatus characterized by the presence of containment element, such as a sealed reservoir applied on sclera (with a semi-permeable membrane on application surface) under the eyelid, that is filled with the medicament released under the influence of the electrical current.

The peculiar feature of the invention described in U.S. Pat. No. 6,442,423 filed on May 2, 1999 is an applicator having a receiving portion holding a replaceable hydrogel carrier that is loaded with the drug. The solution provided by this invention ensures that the fluid drug solution is maintained in contact with the eye during the iontophoresis process, in fact handling of fluids to ensure their contact with eye surface is tricky, since fluids leak and form bubbles that reduce the efficacy of iontophoretic process.

The invention described in U.S. Pat. No. 6,154,671 filed on Apr. 1, 1999 relates to a device for transferring active pharmaceutical ingredients into the eyeball by iontophoresis characterized by an active electrode in the reservoir which is a surface electrode arranged facing eye tissues lying at the periphery of the cornea. In this case the transfer achieved by this system takes place through one or more eye tissues lying at the periphery of the cornea over a wide application area.

The matter of the invention disclosed by U.S. Pat. No. 7,164,943 filed on Mar. 6, 2004 relates an irritation-reducing ocular iontophoresis device provided by such features enabling to reduce application time on the eye and consequent irritation.

Furthermore, following technical advances in the iontophoresis field in the last decades occurred, in particular concerning devices and apparatus, currently in research and development and mainly focused on several formulations suitable for delivery by ocular iontophoresis and methods of use thereof.

Use of ophthalmic compositions, possibly associated to riboflavin for corneal cross-linking in the treatment of keratoconus or other corneal ectasic disorders have been described and is matter-subject of the international patent application PCT/IT2009/000392, and relative priority patent application RM2008A00472. Such disclosed riboflavin based compounds facilitate epithelial absorption associated to corneal CXL, avoiding the resort to de-epithelization of the cornea, enabling a non-invasive corneal elimination or reduction of the anaesthesia and consequent fast healing without pain or possible complication for the patients.

It is also known, from WO2007/025244, a kit cleaning system and method is disclosed. One embodiment of the present invention has a photosensitizer solution supplied by a pressurized nozzle to the target site. Specific application of the solution is to an oral or skin surface target site. The photosensitizer solution is illuminated with sensitizing light creating reactive chemical species. Pressure and a solvent having an elevated concentration of oxygen or oxygen species improve the efficiency of the killing of pathogens. Methods of using the system within an oral cavity are also disclosed.

In this document, the active electrode is not transparent to UV light, visible light or IR light.

However, despite the more recent advances in the relevant field, there is still the need of more efficient delivery systems for releasing ophthalmic compositions to imbibe corneal stroma in the practice of corneal cross-linking for the treatment of keratoconus, and of suitable ophthalmic compositions for the treatment of keratoconus specifically formulated to be adapted to the more efficient corneal iontophoresis application as well.

BRIEF SUMMARY OF THE INVENTION

Described in the following are new devices and new method utilizing iontophoresis to actively deliver a compound based on riboflavin into a mammalian eye. The method and device according to the present invention focus on developing riboflavin formulations and uses thereof to be employed in performing CXL to treat keratoconus.

BRIEF DESCRIPTION OF THE DRAWINGS

FIG. 1 schematically shows a preferred embodiment of the present invention;

FIG. 2 shows a detail of FIG. 1;

FIGS. 3A, 3B and 3C show, respectively, three different structures for the active electrode;

DETAILED DESCRIPTION OF THE PREFERRED EMBODIMENTS

Figure 4:
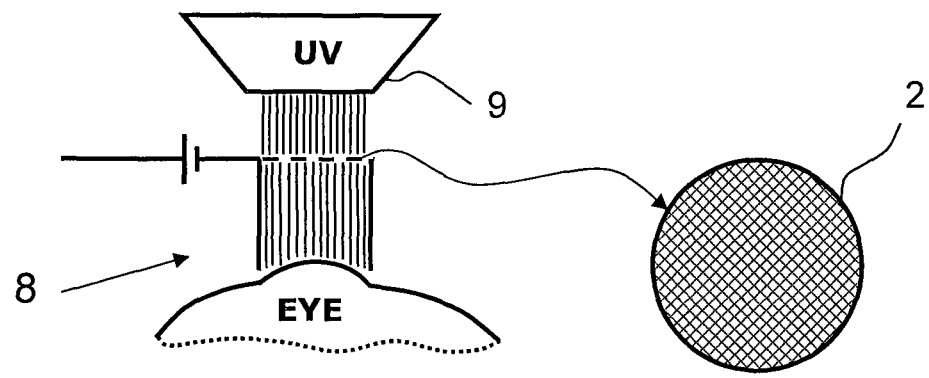
FIG. 4 shows a particular embodiment of the present invention in which the electrode structure has as a mesh or surface including a sufficient number of holes so the electrode is semi-transparent to UV at the appropriate wavelength of 365 nm.

Riboflavin sodium phosphate, commonly used in corneal cross-linking, is a low molecular weight, water soluble, negatively charged molecule; such set of features makes it potentially a suitable target for cathodic iontophoresis as shown in FIG. 1.

As already indicated above, iontophoresis is substantially the promotion of the movement of a charged substance across a biological membrane by the application of a low electrical current forming an electrical field; it is the result of 3 transport mechanisms: chemical, electrical and electroosmotic fluxes which are explicited in the Nernst-Planck equation below:

$$Flux_{total} = Flux_{passive} + Flux_{electric} + Flux_{osmotic}$$

$$Flux_{total} = -D/(dc/dx) + (D.z.V.F.Ci)/(k.T) +/- C.u$$

Where:
D Diffusion coefficient (characteristic of the biological membrane)
dc/dx Concentration gradient
z valence
V Electrical field
F Faraday's constant
k Boltzmann's constant
T Temperature
Ci Ionized drug concentration
C Drug concentration
u convective flow of water We assume, for simplicity, that the passive contribution is negligible (see Prausnitz "Permeability of Cornea, Sclera, and Conjunctiva: A Literature Analysis for Drug Delivery to the Eye", Journal of Pharmaceutical Sciences/1479 Vol. 87, No. 12, December 1998 for experimental values).

Electrorepulsion flow depends on charge (valence), electrical field V and concentration Ci, which are proportional to current density I and inversely proportional to ions mobility in fluid u (I=u.z.V.Ci). Ion mobility depend upon several factors as concentration, interaction between, ionic species themselves and between the ions and the solvent molecule, size of the charged drug molecule, polarity of the solvent, . . . etc Electroosmotic flow occurs when an electrical field is applied across a membrane and produces bulk motion of the solvent itself that carries ionic or neutral species with the solvent stream. It is proportional to concentration of both ionic and neutral species of the drug.

From this, we can simplify Nersnt-Planck equation as follow:

$$Flux_{total} = +(D.I.Ci)/(u.k.T) +/- C.u$$

One of the concern is the electroosmotic flow direction and the relative importance of the flow as compared with repulsion and passive flow. The electroosmotic flow is in the direction of the membrane charge's counter-ions. At physiological pH (7.4), skin, like most of the biological membranes including cornea and sclera is negatively charged. Therefore, the electroosmotic flow enhance anodic (+) delivery of positively charged drug while cathodic (−) of negatively charged drug delivery is retarded.

At low pH, over pI, isoelectric value of the cornea and sclera considered to be 4 (see Huang et al, Biophysical journal 1999) and comparable to skin surface's pI values that ranges from 3 to 4, the surface turns positive and electroosmotic flux reverses. That explains the importance of buffering, which besides the fact it protects conjunctival and corneal damage (eye can tolerate a fairly wide pH range and ophthalmic solutions may range from pH 4.5-11.5, but the useful range to prevent corneal damage is 6.5 to 8.5), but it keeps the relative contribution of each flow at a constant level. It also guaranties a stable number of ionic species in the solution if the duration of applied current is kept short.

In view of the above, it is an object of the present invention to provide an innovative iontophoresis device for delivering a specific product formulation adapted to corneal imbibition associated to CXL and subsequent UV treatment for obtaining cross-linking of corneal stroma proteins.

Another object of the invention is to propose an ocular iontophoresis method using said innovative device with an optimized riboflavin solution in a form that is more easily ionizable and such as to maximize its introduction through cornea by iontophoresis and to dramatically reduce the needed treatment time.

This ocular iontophoretic based approach is a novel, non-invasive, and a much more efficient method which can lead to better results than those achieved by classical riboflavin administration ways to introduce riboflavin to the cornea to be treated by CXL. Remarkably, as the administration time is significantly reduced due to increased transfer efficiency, the procedure results much more comfortable for patients.

Thus, in a first aspect the herewith presented invention is an ocular iontophoresis device for delivering riboflavin solution to the cornea, the device comprising:

a reservoir containing the riboflavin solution which is suitable to be positioned on the eye;
an active electrode disposed in the reservoir; and
a passive electrode.

The passive electrode is placed on the skin of the subject, elsewhere on the body, preferably in close vicinity of the eye, such as forehead, cheeks or neck.

There is also provided a method of treatment of keratoconus by ocular iontophoresis, wherein in order to deliver riboflavin solution to perform corneal cross-linking, a iontophoretic device is positioned on the eye, the device comprising a reservoir containing the riboflavin solution with an initial pH around 4-5, without buffer or a minimal buffer content, the reservoir being suitable to be positioned on the eye, and having an active electrode placed in the reservoir, and a passive electrode; the solution movement is driven by a cathodic current applied for 0.5 to 5 min, preferably 1 to 3 min, at an intensity of 2 mA, preferably 1 mA.

Furthermore, in a third aspect there is provided an ocular iontophoresis device comprising:
a) a reservoir containing the riboflavin solution, the reservoir extending along a surface intended to cover a portion of the eyeball surface and provided with a flushing element to remove excess of riboflavin solution at the end of the iontophoresis procedure,
b) an active electrode structure made of material transparent to UV light associated with the reservoir so as to supply an electric field directed through the riboflavin solution and toward a surface of the eye wherein the riboflavin solution is transcorneally delivered through the surface of the eye by iontophoresis, the material transparent allowing the irradiation of the riboflavin solution immediately following current application.

According to the present invention the electrode structure is made of electrically conductive material, such as stainless steel, ferrous materials, non-ferrous materials such as aluminum, copper, tungsten, silver, gold, carbon, conductive polymers (naturally conductive or loaded with conductive particles).

Electrode can be either made of a mesh, a plate pierced with pinholes or any semi-continuous structure with holes, large enough to allow UV light to be transmitted.

Ideally, the electrode can be made of a continuous transparent plastic part, plated on the reservoir side with a mesh or with thin lines of conductive materials, that can be printed using serigraphy or pad-printing techniques.

Electrode is connected to a continuous current generator delivering a continuous 0.5 to 2 mA current at a voltage adapted to the body and riboflavin solution impedance. The generator is in turn connected to a return electrode placed elsewhere on the body to close the electrical circuit.

The device electrode is ideally placed at a distance of 1 to 6 mm to the central cornea, or preferably at a distance of 4 to 5 mm.

From the experimentation, it has be noted that, during the iontophoresis application time, the pH increases only at the vicinity of the electrode and therefore away from the eye surface. As a consequence, according to the present invention, the value of pH shift at the eye surface can be controlled by modifying the distance of the electrode from the eye surface.

The distance of the electrode from the eye surface is increased for a longer iontophoretic application time, thus minimizing the increase of pH at the eye surface.

In a particular embodiment of the present invention the electrode structure has as a mesh or surface comprising a sufficient number of holes so the electrode is semi-transparent to UV at the appropriate wavelength of 365 nm (FIG. 4).

Figure 5:
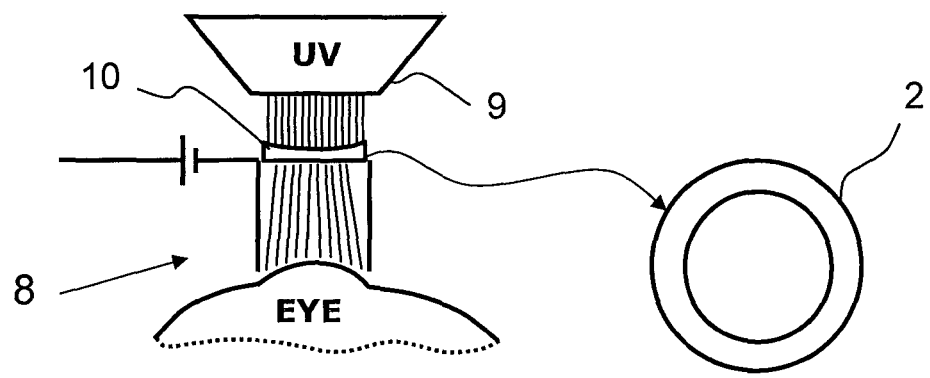
FIG. 5 shows another particular embodiment in which the electrode structure has an annulus shape, having in its center a divergent transparent lens allowing an illumination surface of diameter 8 mm at a distance of 10 mm.

In another particular embodiment the electrode structure has an annulus shape, having in its center a divergent transparent lens allowing an illumination surface of diameter 8 mm at a distance of 10 mm (FIG. 5).

Figure 6:
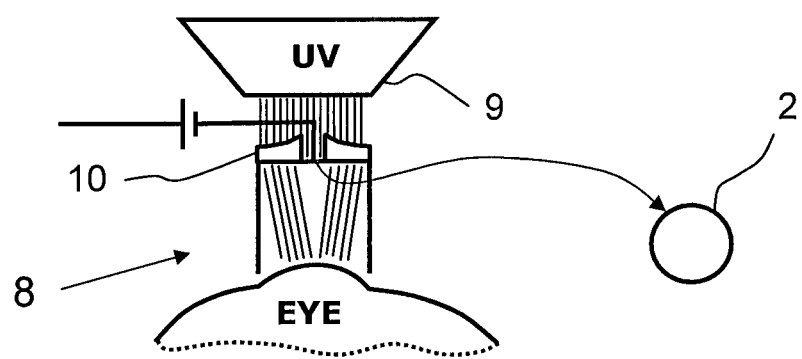
FIG. 6 shows a further particular embodiment in which the electrode structure is a disk, surrounded with a divergent annular lens allowing an illumination surface of diameter 8 mm at a distance of 10 mm.

In another particular embodiment the electrode structure is a disk, surrounded with a divergent annular lens allowing an illumination surface of diameter 8 mm at a distance of 10 mm (FIG. 6).

Figure 7:
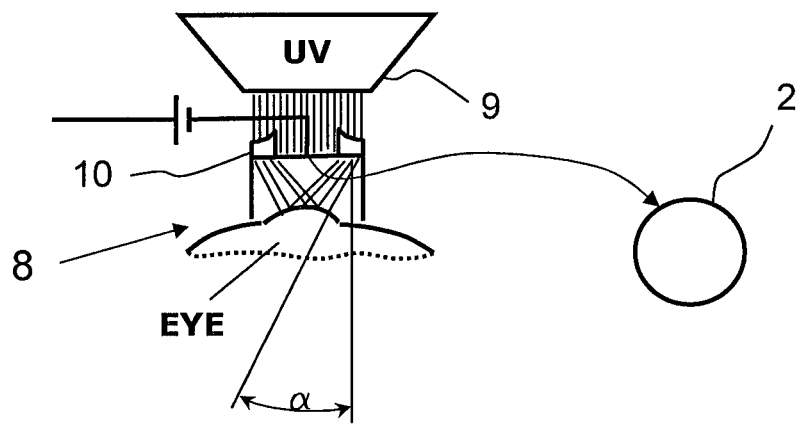
FIG. 7 shows a variant of the present invention wherein the electrode structure is a disk of diameter 10 mm, surrounded with a divergent annular lens allowing an illumination surface of diameter 8 mm at a distance of 10 mm, the walls of the device having an angle of alpha, which is between 60° and 20°, preferably between 30° and 20° to avoid excessive incident light refraction.

In another variant the electrode structure is a disk of diameter 10 mm, surrounded with a divergent annular lens allowing an illumination surface of diameter 8 mm at a distance of 10 mm, the walls of the device having an angle of alpha, which is between 60° and 20°, preferably between 30° and 20° to avoid excessive incident light refraction (FIG. 7).

According to the present invention the iontophoresis device has circular shape with inside diameter of 8-12 mm, preferably 10 mm, made of non-electrically conductive materials, such as plastic. The proximal side of the device, that in contact with the corneal or limbus at the periphery of the cornea, can be made of a different material, such as an elastomeric material, this feature allows to accommodate small changes in eye geometry so it can fit perfectly on eye's surface avoiding fluid leaks.

At the periphery of the device structure, a second circular wall with an open end on eye's side and a close end on electrode side and means to form a light vacuum in the outer annular chamber (see FIG. 1).

The distal surface of this annular chamber corresponds to the pars plana area of the eye, with an internal diameter of 12 mm and an external diameter of 18 mm, preferably 16 mm, or more preferably 14 mm.

When device in place on the eye, a light vacuum is set in this chamber to hold the device in place during application.
Electrode Structure:

Same plastic transparent material, such as polymethacrylate, polycarbonate, cycloolefin, polymethylpentene, polystyren is used to shape a divergent or convergent lens allowing central corneal illumination of a diameter 8 to 10 mm.

Lens can be placed centrally or peripherally on the electrode, or around the electrode. When the lens is placed around the electrode, the electrode surface is maximized.

The device structure with its walls and the electrode forming a reservoir, with an open end being in contact with the eye and a closed end where the electrode is located.

Advantageously, walls of the device can be made with a non-transparent material at the given treatment wavelength to avoid irradiation of the periphery of the cornea or limbal structure.

The application time of the device on the cornea consist in 0.5 to 5 min application of current, immediately followed by UV irradiation time of 5 to 30 min at a power of 3 to 30 mW/cm$^2$.

Before application of light, the Riboflavin content in the reservoir is purged.

Finally, it is useful to point out that the device according to the present invention can be applied to any ionized solution, positively or negatively charged, that would induce collagen cross-linking upon application of UV light and/or visible light and/or IR light.

LIST OF REFERENCES IN THE DRAWINGS 1. inner wall
2. active electrode 3. annular chamber
4. spring
5. syringe
6. non return valve
7. transparent plastic
8. reservoir
9. means for irradiating the cornea surface
10. lens

The invention claimed is:

1. An ocular iontophoresis device for delivering any ionized drug solution, such as riboflavin solution, to the cornea, the device comprising:
   a reservoir containing a riboflavin solution which is suitable to be positioned on the eye;
   an active electrode disposed in or on the reservoir;
   a passive electrode configured to be placed on the skin of the subject, elsewhere on the body, preferably in close vicinity of the eye;
   an irradiation device configured to irradiate the cornea surface with light to obtain corneal cross-linking after the delivering of Riboflavin;
   wherein said reservoir and said active electrode are transparent to one or more of ultraviolet (UV) light, visible light, and infrared (IR) light.

2. The device according to claim 1, further comprising a current device configured to provide a cathodic current having an intensity of 2 mA, preferably 1 mA.

3. The device according to claim 1, further comprising a current device configured to provide a cathodic current for 0.5 to 5 min, preferably 1 to 3 min.

4. The device according to claim 1, wherein said reservoir containing the riboflavin solution extends along a surface covering a portion of the eyeball surface and is provided with a flushing element to remove excess riboflavin solution at the end of the iontophoresis procedure.

5. The device according to claim 1, wherein said active electrode has a structure made of a material transparent to the UV light associated with the reservoir to supply an electric field directed through the riboflavin solution and toward a surface of the eye, the riboflavin solution being transcorneally delivered through the surface of the eye by iontophoresis, the transparent material being configured to allow the irradiation of the riboflavin solution immediately after the end of a current application.

6. The device according to claim 1, wherein the electrode has a discontinuous structure made of electrically conductive material including one or more of stainless steel, ferrous materials, non-ferrous materials such as aluminum, copper, tungsten, silver, gold, carbon, conductive polymers naturally conductive or loaded with conductive particles.

7. The device according to claim 6, wherein said electrode is made of a mesh, or a pierced plate or any semi-continuous structure with openings large enough to allow the UV light to be transmitted.

8. The device according to claim 6, wherein said electrode is constituted by a continuous transparent plastic part which is provided on the reservoir side with a plated mesh or with plated thin lines of conductive materials, the plated mesh or the plated thin lines of conductive materials being printed using serigraphy or pad-printing techniques.

9. The device according to claim 1, wherein said electrode is connected to a continuous current generator delivering a continuous 0.5 to 2 mA current at a voltage adapted to the body and riboflavin solution impedance, said generator being connected to said return passive electrode placed elsewhere on the body to close the electrical circuit.

10. The device according to claim 1, wherein the device is placed at a distance of 1 to 6 mm to the central cornea, or preferably at a distance of 4 to 5 mm.

11. The device according to claim 1, wherein the electrode structure is a mesh or a surface comprising a sufficient number of holes so the electrode is semi-transparent to UV light at a wavelength of 365 nm.

12. The device according to claim 1, wherein the electrode structure has an annulus shape, having in its center a divergent transparent lens allowing an illumination surface of diameter 8 mm at a distance of 10 mm.

13. The device according to claim 12, wherein a plastic transparent material, such as polymethacrylate, polycarbonate, cycloolefin, polymethylpentene, or polystyrene, is used to shape a divergent or convergent lens allowing central corneal illumination of a diameter 8 to 10 mm.

14. The device according to claim 1, wherein the electrode structure is a disk, surrounded with a divergent annular lens allowing an illumination surface of diameter 8 mm at a distance of 10 mm, the lens being placed around the electrode, the electrode surface not being impeded.

15. The device according to claim 1, wherein the electrode structure is a disk of diameter 10 mm, surrounded with a divergent annular lens allowing an illumination surface of diameter 8 mm at a distance of 10 mm, the device having walls placed with an angle of alpha.

16. The device according to claim 15, wherein the angle alpha is between 60° and 20°, preferably between 30° and 20°, to avoid excessive incident light refraction.

17. The device according to claim 1, wherein the device has a circular shape with an inside diameter of 8-12 mm, preferably 10 mm, made of non-electrically conductive materials, such as plastic.

18. The device according to claim 1, wherein the device has a proximal side configured to be placed in contact with the corneal or limbus at the periphery of the cornea, said proximal side being made of a different material, such as an elastomeric material, thereby accommodating small changes in eye geometry so the device is configured to fit perfectly on the eye surface to avoid fluid leaks.

19. The device according to claim 1, wherein the reservoir has an annular shape, the device including a second circular wall at the periphery thereof, the second circular wall having an open end on the side of the eye and a close end on an electrode side, to form an outer annular chamber for the reservoir,
   the device further comprising a vacuum system configured to form a vacuum in the outer annular chamber to hold the device in place on the eye during application.

20. The device according to claim 19, wherein a distal surface of said annular chamber corresponds to the pars plana area of the eye, with an internal diameter of 12 mm and an external diameter of 18 mm, preferably 16 mm, or more preferably 14 mm.

21. The device according to claim 1, wherein the device has a structure with walls that, together with the active electrode, form the reservoir with an open end configured to come into contact with the eye and a closed end at which the electrode is located.

22. The device according to claim 1, further comprising a purging system configured to purge the reservoir from its content before the application of the UV light or of other suitable light for cross-linking.

23. The device according to claim 1, wherein a distance of the electrode itself and the eye surface is modified to control the value of pH on the eye, as, during the iontophoresis, the pH increases only in proximity to the electrode and therefore away from the eye surface.

24. The device according to claim 1, wherein at least one of a plurality of walls of the device are made with a non-transparent material at a given treatment wavelength to avoid irradiation of the periphery of the cornea or limbal structure.

25. A method for delivering any ionized drug solution, such as riboflavin solution, to the cornea for treatment of keratoconus or any other ectasic corneal disease, or for reinforcing corneal stromal structure by the ocular iontophoresis device according to claim 1, the method comprising:

positioning said iontophoretic device on the eye to be treated, the device comprising a reservoir containing the riboflavin solution;

driving the solution movement by a cathodic current applied for 0.5 to 5 min, at an intensity not higher than 2 mA; and irradiating, immediately after the end of the current application, of the cornea surface with an ultraviolet (UV) light for 5 to 30 min at a power of 3 to 30 mW/cm$^2$, thereby obtaining the corneal cross-linking of the riboflavin.

26. The method according to claim 25, wherein a riboflavin solution having an initial pH of about 4-5 is used, without buffer or with a minimal buffer content.

27. The method according to claim 25, wherein said cathodic current is applied for 1 to 3 min.

28. The method according to claim 25, wherein said cathodic current is applied at an intensity of 1 mA.

29. The method according to claim 25, further comprising, before the application of UV light, purging of the reservoir from riboflavin content.

* * * * *